United States Patent
Fujii et al.

[11] Patent Number: 5,163,437
[45] Date of Patent: Nov. 17, 1992

[54] OPHTHALMIC MEASURING DEVICE

[75] Inventors: Hitoshi Fujii, Munakata; Takashi Yokokura, Tokyo, both of Japan

[73] Assignee: Topcon Corporation, Tokyo, Japan

[21] Appl. No.: 689,881

[22] PCT Filed: Sep. 26, 1990

[86] PCT No.: PCT/JP90/01237

§ 371 Date: May 21, 1991

§ 102(e) Date: May 21, 1991

[87] PCT Pub. No.: WO91/04705

PCT Pub. Date: Apr. 18, 1991

[30] Foreign Application Priority Data

Sep. 26, 1989 [JP] Japan ................... 1-249722

[51] Int. Cl.⁵ .............................................. A61B 5/02
[52] U.S. Cl. .................................... 128/665; 128/691
[58] Field of Search ............... 128/664, 665, 661.07, 128/691; 606/4

[56] References Cited

U.S. PATENT DOCUMENTS

| | | | |
|---|---|---|---|
| 4,166,695 | 9/1979 | Hill et al. | 128/691 |
| 4,346,991 | 8/1982 | Gardner et al. | 128/691 |
| 4,579,430 | 4/1986 | Bille | 128/691 |
| 4,743,107 | 5/1989 | Aizu et al. | 128/691 |
| 4,848,897 | 7/1989 | Aizu et al. | 128/691 |
| 4,950,070 | 8/1990 | Aizu et al. | 128/691 |
| 4,952,050 | 8/1990 | Aizu et al. | 128/691 |

*Primary Examiner*—Lee S. Cohen
*Assistant Examiner*—J. Jastrzab
*Attorney, Agent, or Firm*—Mason, Fenwick & Lawrence

[57] ABSTRACT

An ophthalmic measuring device is used for measuring blood flow at a fundus to be subjected to ophthalmic examination. The device includes and illumination system for illuminating the fundus to be examined, a projection system for irradiating a predetermined area of the fundus with a measuring laser beam, a detection device for detecting a reflected measuring laser beam reflected from the irradiated area, a storage device for storing signals obtained by the detection device, and an arithmetic processing section for arithmetically processing blood flow in a blood vessel of the fundus based on the stored signals. The device has the capability of indicating an area to be detected on the fundus. The device allows a photograph of the fundus to be taken, superimposed on an image of the indicated area, substantially simultaneously with the storage of the signals in the storage device.

1 Claim, 5 Drawing Sheets

OPHTHALMIC MEASURING DEVICE

FIELD OF THE INVENTION

The present invention relates to an ophthalmic measuring device for measuring blood flow at a fundus to be subjected to ophthalmic examination.

When a laser beam is directed upon a tissue of a living body such as a fundus to illuminate thereon, the laser beam is scattered by particles which are present in the tissue of the living body, the scattered rays interfere with each other, causing a random pattern of the reflected scattered rays, i.e., a speckle pattern. On the other hand, as this speckle pattern varies momentarily with movement of blood cells as such particles in a blood capillary, by measuring change with time in light intensity at a certain point light signals are obtained including information concerning blood flow velocity, i.e., speckle signals. The present invention is directed to an ophthalmic measuring device for measuring a fundus with respect to blood flow velocity by utilizing the speckle pattern.

RELATED ART

Heretofore, there has been known an ophthalmic measuring device designed such that it illuminates a fundus to be examined with laser beam, photoelectrically detects the reflected light, and, based on the detected signals, measures blood flow velocity in a blood vessel at the fundus to be examined. A device of this type is arranged such that an illumination system and a detection system for a laser beam are incorporated into a conventional fundus camera, and, by means such as changing a direction of a visual axis of a subject while observing a fundus to be examined, a desired area of a blood vessel is illuminated with a laser beam to perform measurement.

Further, such a device is arranged such that the state of a fundus to be examined is photographed to record the state of the eye subjected to measurement.

However, as there are continual slight tremors of a collimation axis so-called flicks in an eye to be examined, an image of the fundus which an ophthalmic examiner observes always slightly oscillates. Consequently, it is difficult for such a conventional device to accurately identify the measured site at a moment when measurement has been conducted, so that there is adverse possibility of measurement at an area other than the intended site.

Further, in this conventional device, a photograph is taken after the measurement to record the area where measurement has been conducted. However, there is a problem in that because of the time lag between the recording and the moment of the measurement, it is difficult to record the exact measured site. Further, the conventional device separately requires the step of photographing besides the measurement, and therefore, the conventional devices are complicated in measuring procedure.

SUMMARY OF THE INVENTION

The present invention has been made in view of these problems. It is, therefore, an object of the present invention to provide an ophthalmic measuring device which is capable of recording an image of a fundus over which an image of an indication indicating a measured area is superimposed.

According to the present invention, there is provided an ophthalmic measuring device comprising:

an illumination system for illuminating a fundus to be examined, a projection system for irradiating the predetermined area of the fundus to be examined with measuring a laser beam, a detection means for detecting a reflected measuring laser beam from the irradiated area, a storage means for storing signals obtained by means of the detection means, and an arithmetic processing section for arithmetically processing state of blood flow in a blood vessel in the fundus on the basis of the stored signals;

Wherein the device indicates an area of the fundus to be examined, and a photograph of an image of the fundus, superimposed on an image of the indication, may be taken substantially simultaneously with the storage of signals into the storage means.

DETAILED DESCRIPTION OF THE PREFERRED EMBODIMENTS

Now, embodiments of the present invention will be described with reference to the drawings.

Figure 1:
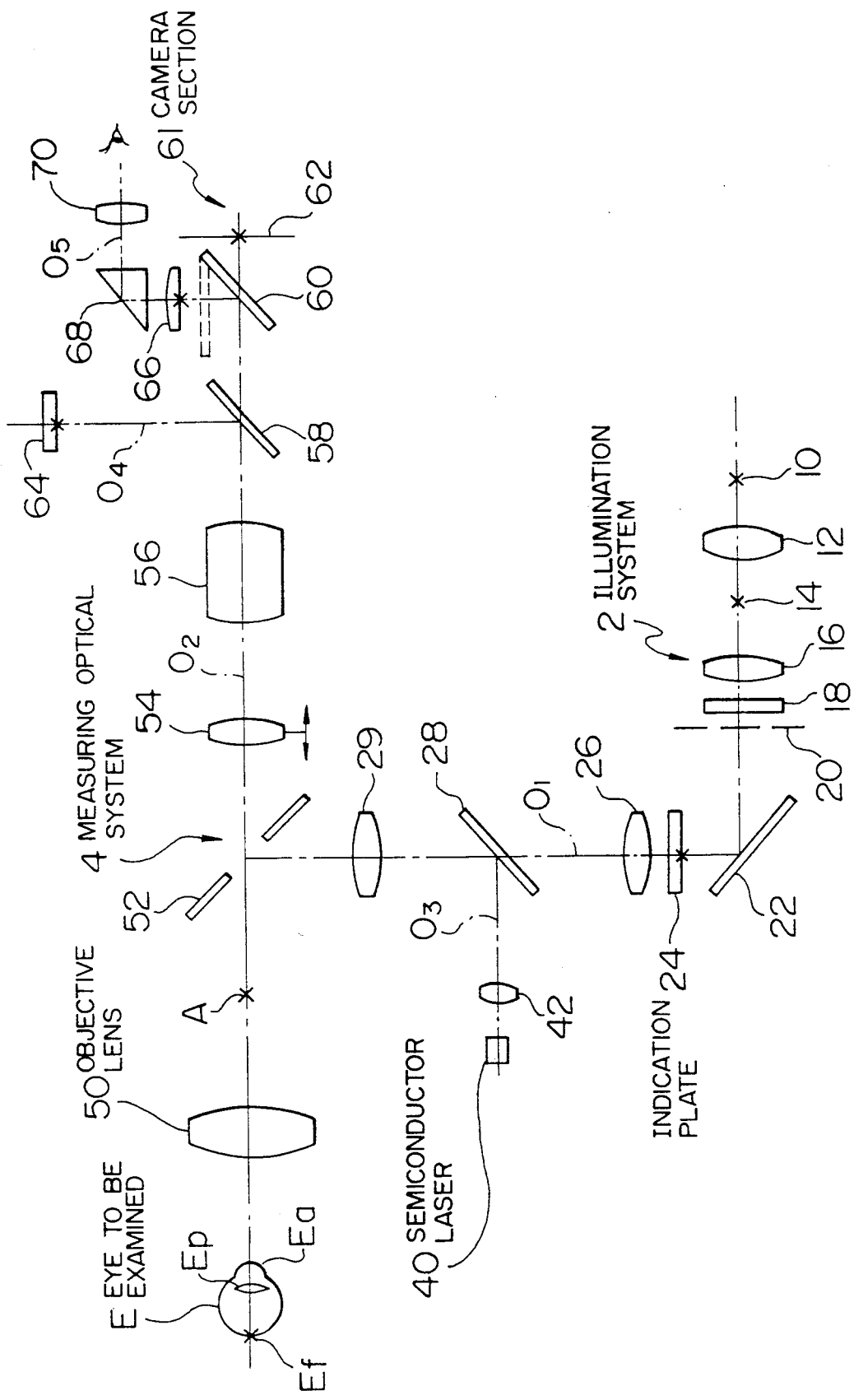
FIG. 1 is an optical view of a mydriatic fundus camera of the first embodiment of the present invention.

With respect to the first embodiment, the present invention was applied to a mydriatic fundus camera. As shown in FIG. 1, illumination system 2 comprises, arranged on illumination light axis $O_1$, an observation light source 10 which radiates visible light, first condenser lens 12, a photographic light source 14 arranged in conjugate relationship to the observation light source 10 with respect to the condenser lens 12, second condenser lens 16, and a filter 18 which does not transmit infrared radiation but transmit visible light, and ring slit 20 as well. This ring slit 20 is disposed in conjugate relationship to a pupil $E_p$ of an eye E to be subjected to ophthalmic examination.

The illumination system 2 further has mirror 22, indication plate 24, first relay lens 26, first dichroic mirror 28 disposed obliquely which reflects infrared rays including ray of 830 nm and transmits visible light, and second relay lens 29.

Figure 2:
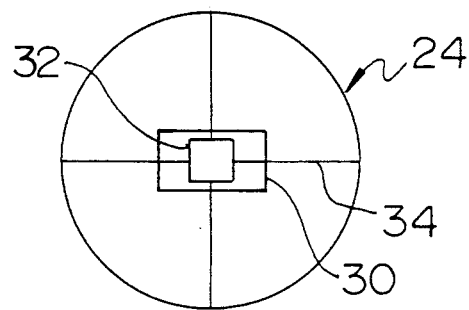
FIG. 2 is a plan view of a collimation.

The indication plate 24 serves to form an indication image indicating the area to be measured on a fundus E $f$ to be subjected to ophthalmic examination. As shown in FIG. 2, the indication plate 24 comprises outer rectangular frame 30 indicating a illumination area of laser beam, inner square frame 32 indicatinq a measurement area, and cross hairs 34 for indicating the center of the indication plate. The indication plate 24 is disposed in conjugate relationship to a fundus E $f$. However, the indication plate may be projected on a fundus E $f$ through a half mirror.

The first dichroic mirror 28 serves to lead a laser beam for blood flow measurement onto the illumination light axis $O_1$. A semiconductor laser 40, and a collimator lens 42 are arranged On light axis $O_3$ of laser beam incident on the first dichroic mirror 28. The semiconductor laser 40 emits infrared laser beam having a wavelength of 830 nm, and is disposed at a position conjugate to a front portion $E_a$ of an eye E to be subjected to ophthalmic examination.

A measuring optical system 4 comprises, arranged on measurement light axis $O_2$ in the following order from the side of the eye E to be subjected to ophthalmic examination, an objective lens 50, a perforated mirror 52, a focusing lens 54, a image forming lens 56, a dichroic mirror 58, a quick return mirror 60, and a film 62. Between the objective lens 50 and the perforated mirror 52, there is a conjugate point A which is conjugate to the fundus $E_f$ with respect to the objective lens 50. The perforated mirror 52 and the front portion $E_a$ of the eye E to be subjected to ophthalmic examination are conjugate to each other with respect to the objective lens 50. The second dichroic mirror 58 has the same structure as that of the first dichroic mirror 28.

On the reflected light axis $O_4$ of the second dichroic mirror 58 is disposed an image sensor 64 in conjugate relationship to the fundus $E_f$. On reflected light axis $O_5$ of the quick return mirror 60 are arranged a field lens 66 formed with the same indication as the indication plate 24, a reflecting prism 68, and an ocular 70. The quick mirror 60, the film 62, the field lens 66 etc. constitute a camera section 61.

In the above-mentioned optical system, observation light beam and photographic light beam which have passed through the ring slit 20 become incident on the periphery of the front portion $E_a$ of the eye to form image of the indication on the fundus $E_f$, and the laser beam having a wavelength of 830 nm emitted from the semiconductor laser 40 also passes through the periphery of the front portion $E_a$ to irradiate the position indicated by the image of the indication on the fundus $E_f$.

Figure 3:
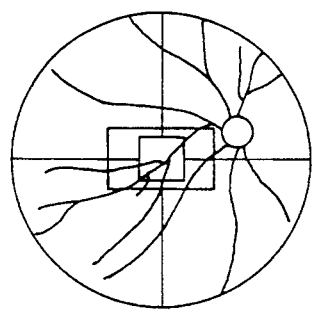
FIG. 3 is a diagrammatic view of an image of a fundus including an image of an indication.

Of the reflected rays, visible light passes through center portion of the front portion $E_a$ of the eye and the aperture of the perforated mirror 52, and forms image of the fundus with the image of the indication which is shown in FIG. 3.

On the other hand, the infrared ray of 830 nm reflected from the fundus $E_f$ is reflected by the second dichroic mirror 58, and forms image on the image sensor 64.

Figure 4:
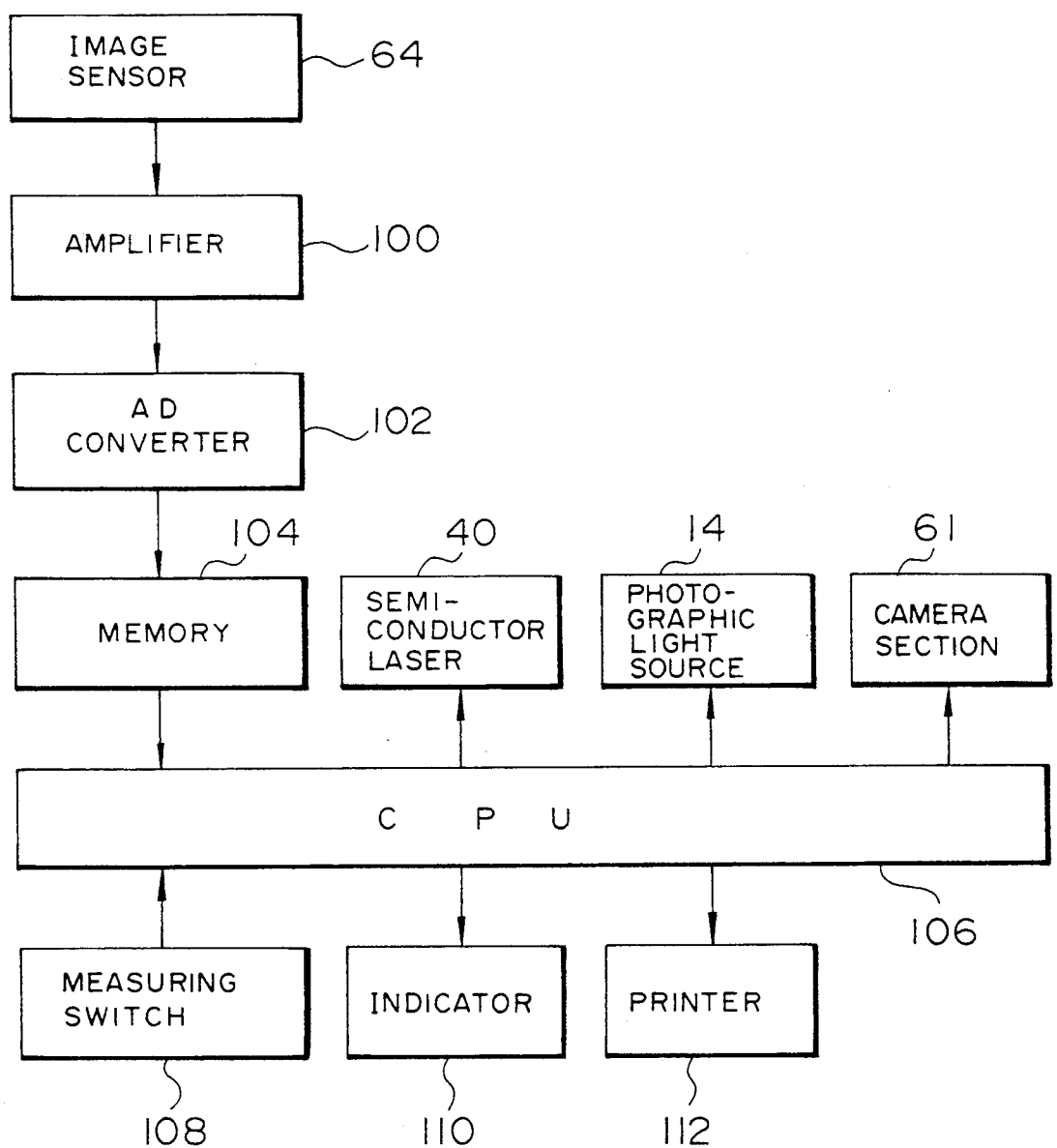
FIG. 4 is a block diagram of a signal processing system of the first embodiment.

FIG. 4 is a block diagram of the circuit of the embodiment of the signal processing system for output from the image sensor 64. The output of the image sensor 64 is connected sequentially a video amplifier 100, an A/D converter 102, a memory 104, and a CPU 106. To the CPU 106 are further connected a measuring switch 108, an indicator 110, the above-mentioned semiconductor laser 40, the above-mentioned photographic light source 14, the above-mentioned camera section 61, and a printer 112. In the above-mentioned setup, when the measuring switch 108 is turned on, the CPU 106 causes the semiconductor laser 40 and the photographic light source 14 to emit rays, and the camera section 61 takes a photograph. On the other hand, scanning output signals, i.e., image signals are amplified by an amplifier 100, digitized by the high speed A/D converter 102, and stored in memory 104 sequentially. In accordance with this procedure, scanning is repeated for 100 to 300 times with respect to the same scanning line at 1.7 $\mu$ sec per one scanning, i.e., about 700 Hz, data are stored, and then each difference between consecutive two scanning outputs is determined in accordance with the program stored in CPu 106. This, in practice, is implemented by the following operation.

The reason for conducting the scanning for 100 to 300 times is that minute oscillation, i.e., tremor is evened off so as to eliminate frequency components of 30 to 100 Hz at about 15 seconds in terms of a visual angle from the collimation axis. Further, oscillation having a frequency corresponding to tremor of about 5 minutes in terms of a visual angle, i.e., drift can be eliminated by measuring at a speed of 1.7 m sec per one scanning.

When for the (m,n)th picture element of image sensor 64 comprising N picture elements, the kth scanning outputs is denoted by $I_k(m,n)$, the (k+1)th output is denoted by $I_{k+1}(m,n)$, output I(m,n) of the (m,n)th picture element is represented by the formula:

$$I(m,n) = \sum_{Km=1}^{N} \frac{|I_K(m,n) - I_{k+1}(m,n)|}{I_K(m,n) + I_{k+1}(m,n)}$$

In the above operational formula, the denominator serves to normarize the output of each of the picture element, thereby factor attributable to the difference in reflectance of vascular site of the $E_f$ is eliminated so that components caused by speckle shift due to blood flow can be educed. The numerator is a function of variation of speckle, blood flow velocity.

Figure 5:
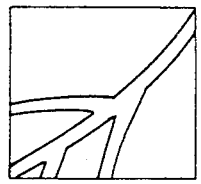
FIG. 5 is an illustration of display with respect to blood flow velocity.

The CPU 106 calculates output with respect to each of the picture elements to detect blood flow velocity two-dimensionally, and as shown in FIG. 5, the blood flow velocity is indicated by the indicator 110 and printed by the printer 112. The indicator 110 and printer 112 are capable of colored two-dimensional indication of the blood flow velocity at the fundus, for example, by showing different colors depending upon the blood flow velocity.

Figure 6:
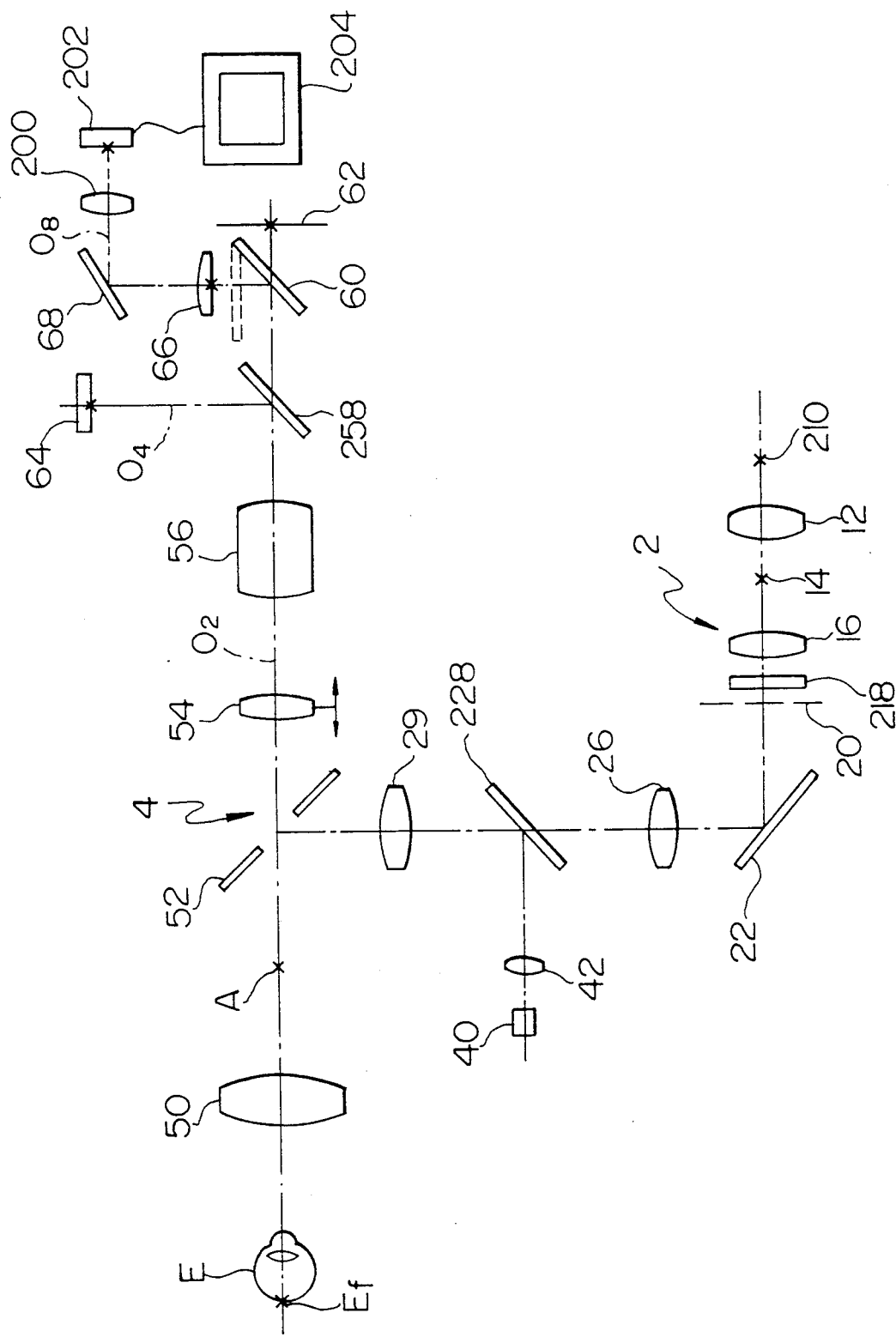
FIG. 6 is an optical view of a non-mydriatic fundus camera of the second embodiment.

The second embodiment, which is directed to a non-mydriatic fundus camera, is shown in FIG. 6. To the like constituents as used in the first embodiment are allotted the like references as used in the first embodiment, and explanation on them is Omitted. The observation light source 210 emits light including infrared rays. On reflected light axis $O_8$ of the quick return mirror 60 are arranged an image forming lens 200, and CCD camera 202 at a position conjugate to the that of the fundus $E_f$, as well as a field lens 66 and a mirror 68. Output of the CCD camera 202 is connected to a television monitor 204. A filter 218 disposed insertably and removably between second a condenser lens 16 and a ring slit 20 has characteristics such that the filter does not transmit visible light, and of infrared rays, only rays within a predetermined width wavelength range centering around the 830 nm, and transmit infrared rays other than the above. The filter is inserted on the light axis during observation and measurement, and removed from the light axis during photographing.

The first dichroic mirror 228 for reflecting a laser beam of 830 nm from the semiconductor laser 40, and the second dichroic mirror 258 for partially reflected light which has passed through the image forming lens 56 on the image sensor 64 have the same optical characteristics, and they reflect only rays within the predetermined width wavelength range centering around the 830 nm and transmit infrared rays other than the above and visible light.

Figure 7:
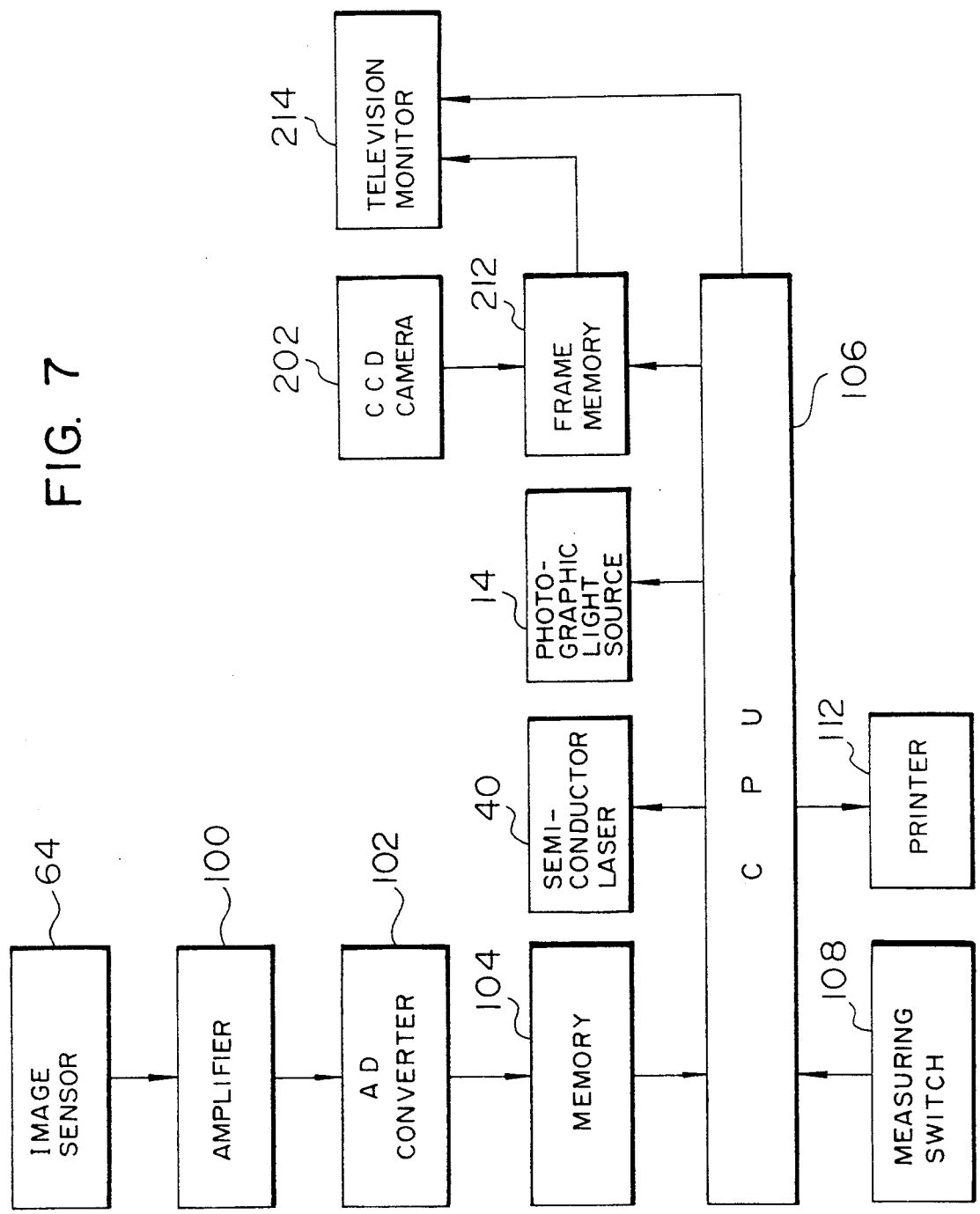
FIG. 7 is a block diagram of a signal processing system of the second embodiment.

As shown in FIG. 7, which is a block diagram of the circuit for the output of the image sensor 64, the output of the image sensor is inputted to a frame memory 212 and television monitor 214 of CPU 106, on the other hand, output of the CCD camera 202 is inputted to the frame memory 212.

In the above-mentioned setup, when the measuring switch is turned on, measurement on blood flow is conducted, and simultaneously therewith, the CCD camera transmits output signal of image of the fundus including image of the indication. The television monitor 214 exhibits a two-dimensional colored display of blood flow velocity with respect to each of picture elements of the image of the fundus, and superimposes the indication-applied image of the area subjected to the blood flow measurement over the display.

We claim:

1. An ophthalmic measuring device, comprising:
   an illumination system means for illuminating a measuring area of a fundus to be examined;
   an irradiating system means for irradiating with a measuring laser beam a predetermined area of the fundus to be examined;
   a measuring area indicating system means for projecting a pattern image to indicate the measuring area;
   fundus image detection means for detecting a reflected measuring laser beam reflected from the irradiated area of the fundus said fundus image detection means providing fundus image detection signals;
   storage means for storing said signals obtained from the fundus image detection means;
   an arithmetic processing section means for arithmetically processing information related to blood flow in a blood vessel of the fundus, on the basis of the signals stored in the storage means; and
   a control system means for controlling the device so that the fundus image detection means provides images of the fundus together with the pattern image formed thereon.

* * * * *